(12) United States Patent
de Vries

(10) Patent No.: US 7,216,761 B2
(45) Date of Patent: May 15, 2007

(54) TWO-COMPONENT MIXING AND DISPENSING DEVICE

(75) Inventor: Jan Albert de Vries, Zelhem (NL)

(73) Assignee: Broockeville Corporation N.V., Willemstad, Curacao (AN)

( * ) Notice: Subject to any disclaimer, the term of this patent is extended or adjusted under 35 U.S.C. 154(b) by 344 days.

(21) Appl. No.: 11/000,578

(22) Filed: Nov. 30, 2004

(65) Prior Publication Data

US 2005/0128868 A1   Jun. 16, 2005

Related U.S. Application Data

(60) Provisional application No. 60/525,917, filed on Dec. 1, 2003.

(51) Int. Cl.
  *B01F 13/00* (2006.01)
(52) U.S. Cl. ............... 206/222; 366/129; 366/139; 366/332; 222/246
(58) Field of Classification Search ............ 604/82–92; 206/222; 222/246; 366/129, 139, 189, 256, 366/332, 333
  See application file for complete search history.

(56) References Cited

U.S. PATENT DOCUMENTS

| 3,760,503 | A | | 9/1973 | Baskas |
| 4,116,240 | A | * | 9/1978 | Guiney ..................... 604/89 |
| 4,159,570 | A | | 7/1979 | Baskas et al. |
| 4,676,406 | A | | 6/1987 | Frischmann et al. |
| 5,252,301 | A | | 10/1993 | Nilson et al. |
| 5,549,380 | A | | 8/1996 | Lidgren et al. |
| 5,551,778 | A | * | 9/1996 | Hauke et al. ............... 366/139 |
| 5,630,800 | A | * | 5/1997 | Blank et al. ................ 604/82 |
| 6,017,349 | A | * | 1/2000 | Heller et al. ............... 606/92 |
| 7,018,089 | B2 | * | 3/2006 | Wenz et al. ............... 366/130 |
| 2003/0012080 | A1 | | 1/2003 | Coffeen et al. |

FOREIGN PATENT DOCUMENTS

| CH | 541 481 | 8/1971 |
| EP | 0 882 436 B1 | 8/2002 |
| WO | WO 01/83094 A1 | 11/2001 |

* cited by examiner

*Primary Examiner*—David Sorkin
(74) *Attorney, Agent, or Firm*—Ryan A. Schneider, Esq.; Troutman Sanders LLP

(57) ABSTRACT

A device for preparing and ejecting polymeric cement made from at least two pre-packaged components comprises a tubular vessel including a first axial end wall having a closed outlet, and a second axial end wall having an aperture. A first starting component of the polymeric cement is present inside said tubular vessel near the first axial end wall. A shaft extends through said aperture of the second axial end wall. A piston element comprises a closed container filled with a second starting component of the polymeric cement. The piston element is selectively lockable to the shaft. The container has a bore and is slidingly engaged upon said shaft. An agitator element is secured to one end of the shaft. Furthermore opening means for providing an opening in the closed container are provided.

Figure 1:
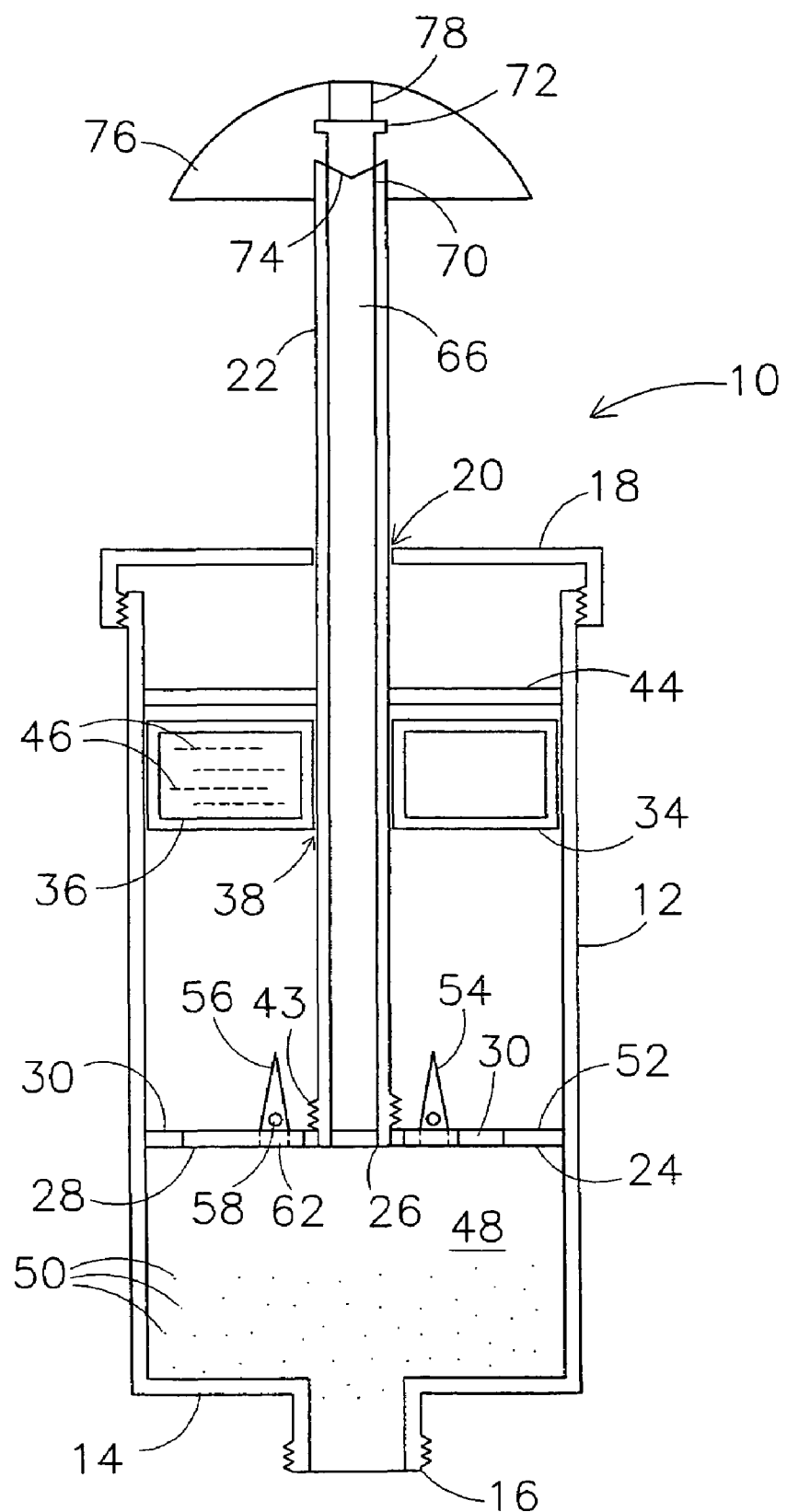

10 Claims, 2 Drawing Sheets

TWO-COMPONENT MIXING AND DISPENSING DEVICE

RELATED APPLICATIONS

This application claims the benefit of U.S. Provisional Patent Application Ser. No. 60/525,917, filed Dec. 1, 2003 entitled A TWO-COMPONENT MIXING AND DISPENSING DEVICE.

TECHNICAL FIELD

The invention relates to a device for preparing and delivering polymeric cement made from at least two pre-packaged components, in particular polymeric cement for use in vertebroplasty. Such polymeric cement is prepared by mixing starting components, most frequently a solid, e.g. powdered polymeric component and a liquid monomer component. After mixing the cement is applied to the location to be treated and allowed to cure. This invention allows the preparation and delivery of polymeric cement in situ, in particular in an operating room environment.

DESCRIPTION OF THE PRIOR ART

Polymeric cement compositions are frequently used in orthopaedic surgery as a bonding material to set implants and artificial joints in bones. The polymeric cement is prepared in the operating room during an operation as needed in view of its fast curing. Various apparatuses and methods for preparing and delivering such cement compositions are known in the art ranging from motorized table-top mixing machines for mixing only to hand-operated devices that fulfill both functions of mixing and delivering.

WO 01/83094 discloses a polymeric bone cement mixing and injection device that is operated by hand. This known device comprises a vessel holding polymer powder and a disk agitator mounted on a shaft passing through an aperture in an end wall of the vessel and extending beyond the agitator through a delivery port in the opposite wall of the vessel. A piston can be selectively coupled to the agitator disk. In order to eject prepared cement, it is necessary to break a distal section of the shaft that passes through the delivery port, mounting the broken off section of the shaft over an external bushing surrounding the delivery port and moving the piston toward the delivery port. In this known device a volume of polymer powder is packed in a sterilized and evacuated vessel, after which the vessel thus filled is packaged in a sterile envelope. The liquid component is drawn into a syringe and then injected through the sterile envelope and an elastomeric, self-sealing diaphragm in the wall of the vessel.

This known device has several drawbacks. First of all, the pre-packaged device comprises only one of the starting components for preparing the polymeric cement. It is still necessary to introduce the other liquid component into the vessel, when polymeric cement is needed. This requires additional actions of the operating staff, as well as careful attention in dosing the appropriate amount of liquid component. Furthermore, after mixing the shaft has to be broken, and attached to the piston in order to eject the cement from the vessel. In fact, two separate handles are needed, one for actuating the agitator element from one side of the device and one for actuating the piston from the other side. Thus operation of this known device is time-consuming and labour-intensive. Moreover there is always a risk that the shaft does not break at the right position, thereby seriously disturbing the action of this device.

EP-B1-0 882 436 has disclosed a transport and process device for two-component material, wherein a liquid starting component and a powder starting component are contained in respective transport chambers separated by a membrane in a closable container. During operation, the membrane is destroyed by a relative movement between the transport chamber for the liquid component and a solid body contained in the container in order to effect a flow of liquid component into the transport chamber of the powder component. Furthermore, the device has an ejection piston at one end of the container opposite to the transport chamber for the liquid component. A manually operated agitator element is situated in the transport chamber for powder component, between the ejection piston and the transport chamber for the liquid. Again the agitator element and ejection piston are operated from different sides by separate mechanisms.

Therefore there is a general need to improve the handling of such devices.

One object of the invention is to provide a device for preparing and ejecting an at least two-component cement, wherein the at least two starting components are pre-packaged, and wherein preparation and ejection are performed by a single shaft.

SUMMARY OF THE INVENTION

According to the invention this object is achieved by a device for preparing and ejecting polymeric cement made from at least two pre-packaged components, said device comprising:

a tubular vessel including a first axial end wall having a closed outlet, and a second axial end wall having an aperture, wherein a first starting component of the polymeric cement is present inside said tubular vessel near the first axial end wall;

a shaft extending through said aperture of the second axial end wall, having a first section outside said vessel and a second section inside said vessel;

a piston element comprising a closed container filled with a second starting component of the polymeric cement, the container having a bore and being slidingly engaged upon the second section of said shaft;

an agitator element mounted on the end of the second section of said shaft;

wherein said piston element is selectively lockable to said shaft; and wherein opening means for providing an opening in said closed container are provided, which opening means are operable by said shaft.

The device according to the invention comprises a tubular body. A first end wall is connected to one end of the tubular body. This end wall is provided with a closed outlet, through which cement is ejected after preparation and removal of the closure from the outlet. A second axial end wall is situated opposite to the first end wall. This second end wall may be a lid or the like, removably connected to the tubular body such as a screw cap. This second end wall is provided with an aperture through which a shaft extends. At the outer end situated outside the tubular body, the shaft is usually provided with a handle in order to improve the grip on the shaft. At the other end situated in the tubular body, the shaft is provided with an agitator element. A piston element is arranged in the tubular body between the agitator element and the second end wall. In addition to its function as ejection piston, this piston element is designed in such a way that it serves as a closed container for pre-packaging one of the starting components of the cement composition to be prepared. This piston element has a bore. The shaft extends through this bore and is displaceable at least to some extent in a first position. In this first position, a relative movement between the piston element and the tubular body is not possible or effectively prevented. In this first position, the piston element, part of the tubular body and the first end wall define a chamber containing the other component of the cement composition. The agitator element is movable between the first end wall and the piston element. The piston element is also lockable to the shaft (a second position). In this second position the piston element can be displaced axially upon movement of the shaft, thereby ejecting the prepared cement through the outlet into the above-mentioned chamber. In order to introduce the component contained in the piston element the device is also provided with opening means for opening the closed container. These opening means are also operable by the shaft.

A significant advantage of the device according to the invention is that subsequent operation of one and the same shaft allows for disrupting the separation between the components, mixing thereof and then ejecting the cement prepared in this way. Another advantage of the device according to the invention is that the starting components of the cement are contained in a pre-packaged manner in appropriate amounts, thus avoiding the need of accurately dosing one or more components when the cement is needed.

The polymeric cement made from the starting components can be used as conventional bone cement. However, the device according to the invention is especially useful in vertebroplasty, e.g. interventional radiology treatment for pain of spinal fractures caused by osteoporosis.

BRIEF DISCUSSION OF THE DRAWING

Figure 2:
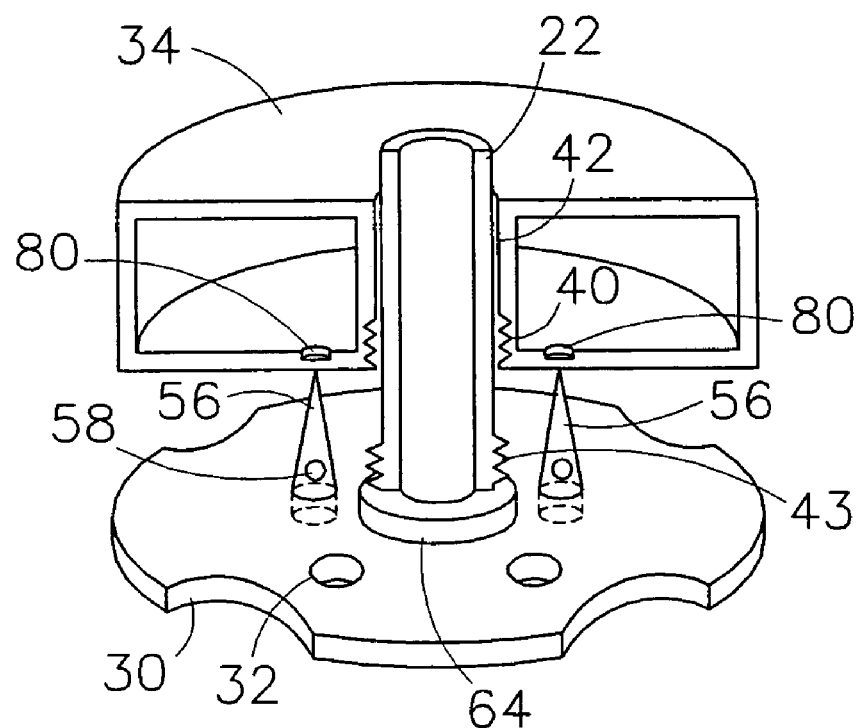
Figure 3:
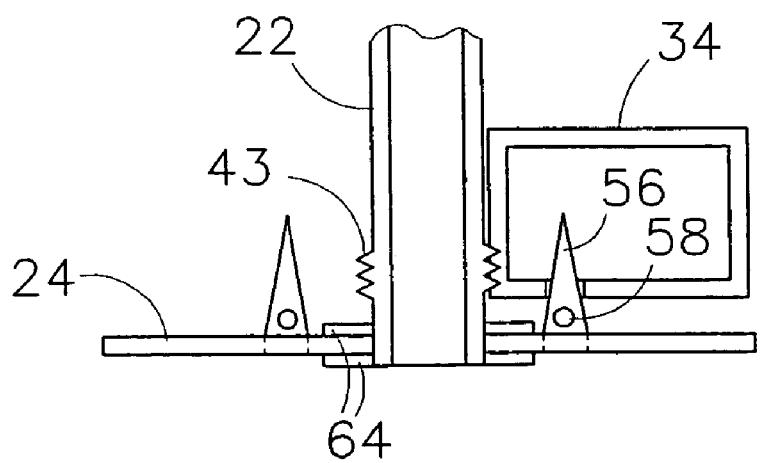

Hereinafter the invention will be illustrated in more detail in view of the accompanying drawings, wherein FIG. 1 shows an embodiment of a device according to the invention in cross-section;

FIG. 2 shows a detail of the embodiment of FIG. 1 in a position for opening the container of the piston element; and FIG. 3 shows a detail of the embodiment of FIG. 1 during ejection.

DETAILED DESCRIPTION OF THE PREFERRED EMBODIMENTS

In a preferred embodiment of the device according to the invention, the shaft is hollow and is provided with a venting port at its outside end. When the cement is prepared from the starting components, noxious gasses may form and create bubbles in the mixture. Or the starting components themselves may be harmful. Furthermore, air bubbles may likewise be included in the preparation as a result of the mixing action. The presence thereof in the final cement is disadvantageous, as these gasses give rise to porosity and reduced strength. In order to prevent the occurrence of these bubbles in the cement mixture, this embodiment of the device according to the invention has a hollow shaft, which is open at the end situated in the tubular body. At the other end the shaft is provided with a venting port for discharging gas. More preferably this venting port is connectable to a vacuum source or other suitable apparatus for generating reduced pressure in the tubular body. The venting port is advantageously provided with a one-way valve.

As already mentioned, the piston element is lockable to the shaft. This may be possible by engagement of the piston element directly by the shaft, or indirectly e.g. by an agitator element which is fixedly connected to the shaft. In a preferred embodiment the bottom part of the bore of the piston element through which the shaft extends is provided with an (inner) screw thread section, while the shaft adjacent the agitator element is provided with a co-operating (outer) screw thread section. In order to mix the components, the shaft and thereby the agitator element is displaced axially. After mixing, the shaft is retracted until the screw thread portions contact each other, and subsequently the piston element is coupled to the shaft by rotating the shaft. Usually the friction of the piston element against the inner wall of the tubular body will be sufficient to withstand the rotational force exerted by the shaft. If needed, additional retaining means may be provided for maintaining the piston element in its position during this step.

In a further preferred embodiment the cross-section of the tubular body of the device according to the invention is non-circular. In such an embodiment the piston element will also have a non-circular cross-section. In this case this non-circular cross-section will prevent radial movement of the piston element with respect to the shaft. More preferably, the cross-section has an elliptical shape.

In yet another preferred embodiment, the opening means comprise at least one puncturing element for puncturing the wall of the container. Such a puncturing element, e.g. a sharp protrusion on that side of the agitator element facing the piston element, allows making one or more holes in the wall of the container wherein one of the starting components is stored, by suitable handling the shaft. This component flows out of the container into the chamber holding the other component. Then the components are mixed thoroughly by moving the shaft and attached agitator element to and fro. Some rotational movement may be performed for increasing the mixing action. More preferably the puncturing element is a hollow needle. Advantageously, the container may be provided with locations having a reduced strength, e.g. a reduced wall thickness, upon which the puncturing elements act. This will increase the reliability of disrupting the separation between the components.

As indicated above, preferably the puncturing element is connected to the agitator element. If there is a risk that the puncturing elements will hold the container wall firmly so that the puncturing elements and piston element will move together from that moment on, in an alternative embodiment the puncturing elements are arranged on a separate plate e.g. disk, slidingly engaed by the shaft, the top of the puncturing elements being directed to the piston element. In this embodiment the opening function to open the container and the mixing function are provided by separate items that are not fixedly connected to one another.

Preferably, the component contained in the piston element is a liquid component, while the component contained in the tubular body itself is a particulate component. Upon rupturing the container wall in an almost vertical position having the outlet opening downwards, the liquid component will flow out the container easily due to gravity or applied vacuum. An example of a polymeric bone cement that can be suitably prepared in a device according to the invention, is acryl based cement.

The attached drawings show an embodiment of a device according to the invention during several stages.

FIG. 1 shows a device for preparing and ejecting polymeric cement made from two components, e.g. a particulate polymer and a liquid monomer. The device indicated in general by reference numeral 10, holds the starting components in separated spaces in appropriate amounts. The device 10 comprises a tubular body 12 having an elliptical cross-section (see FIG. 2) and a first axial end wall 14. The first end wall 14 is provided with an outlet 16, onto which a closure or a suitable nozzle (not shown) can be fitted by means of a screw thread connection. A second axial end wall, in this embodiment a screw cap 18 having an internal screw thread portion is mounted on the other end of the tubular body 10 opposite to the first axial end wall 14. The screw cap 18 has a central aperture 20. A shaft 22 extends through the aperture 20 from the outside into the tubular body 12. An agitator element 24 is mounted at the inner end 26 of this shaft 22. The agitator element 24 comprises a disk 28 having recesses 30 in its periphery, as well as holes 32, which allow passing the mixture from one side to the other. A piston element 34 is arranged between the agitator element 24 and the screw cap 18. The piston element 34 comprises an annular container 36 having a central bore 38. The bore 38 has an inner screw thread section 40 (see FIGS. 2 and 3) at its bottom, and a generally smooth upper section 42, which slidingly engages the shaft 22 in the position shown in FIG. 1. The shaft 22 comprises a co-operating threaded section 43 adjacent the agitator element 24. A sealing gasket 44 is provided on top of the piston element 34. The dimensions of the piston element 34 have been designed such that the piston element 34 fits into the tubular body 12 and retains its position thereby. The container 36 contains a liquid monomer (indicated by short lines 46) as one of the starting components for the polymerization reaction in order to prepare cement. A part of the tubular body 12 together with the first axial end wall 14 and the piston element 34 define a chamber generally indicated by reference numeral 48, wherein powder particles 50 of a polymer as the other starting component are contained. The side 52 of the agitator element 24 facing towards the piston element 34 supports opening means 54, which are in this case hollow needles 56 having an opening 58 in the peripheral wall 60 and an open bottom end 62. The agitator element 24 is mounted between two annular plates 64 fixed to the shaft 22. See FIG. 2. The annular plates 64 have a smaller radius than the agitator element 24 itself so that the recesses 30 and holes 32 remain open. The shaft 22 comprises an axial channel 66 extending between an open bottom end 26 and a top end 70 which is provided with a vacuum port 72 having a one-way valve 74. This vacuum port 72 is arranged in handle 76. A snap connection 78 for fast connection to a vacuum source is mounted onto the vacuum port 72. Generally the device 10 having the pre-packaged components 46 and 50 will be packaged itself in a suitable pliable and sterile envelope.

When polymeric cement is needed, this envelope is removed. If the shaft was locked during transport and storage, this lock is released. By operating the handle 76, the shaft 22 is drawn outwardly. Thereby the agitator element 24 is displaced in the same direction, as a result of which the hollow needles 56 puncture weakened spots 80 in the bottom of the container 36 allowing the liquid monomer contained in the container 36 to flow into the chamber 48. See FIG. 2. The shaft 22 is then displaced to and fro for a number of times, thereby intimately mixing the liquid monomer 46 and polymer particles 50. When the mixture thus prepared is needed, the shaft 22 is again retracted until the screw thread portion 43 of the shaft 22 contacts the corresponding screw thread portion 40 of the bore 38. Then the operator performs a rotational movement of the shaft 22, thereby screwing the piston element 34 onto the shaft 22. See FIG. 3. As the tubular body 12 has an elliptical cross-section in this embodiment, rotational movement of the piston element 34 together with the shaft 22 is not possible. Once the shaft 22 is fastened to the piston element 34, the cement mixture can be pressed through the outlet 16 in the first end wall 14 after replacement of the outlet cap by a suitable nozzle.

What is claimed is:

1. A device for preparing and ejecting polymeric cement made from at least two pre-packaged components, said device comprising:

a tubular vessel including a first axial end wall having a closed outlet, and a second axial end wall having an aperture, wherein a first starting component of the polymeric cement is present inside said tubular vessel near the first axial end wall;

a shaft extending through said aperture of the second axial end wall, having a first section outside said vessel and a second section inside said vessel;

a piston element comprising a closed container filled with a second starting component of the polymeric cement, the container having a bore and being slidingly engaged upon the second section of said shaft;

an agitator element mounted on the end of the second section of said shaft;

wherein said piston element is selectively lockable to said shaft; and wherein opening means for providing an opening in said closed container are provided, which opening means are operable by said shaft.

2. A device according to claim 1, wherein said shaft is hollow, and is provided with a venting port.

3. A device according to claim 1, wherein the shaft is provided with a screw thread section near the agitator element, and the bore of the container is also provided partly with a co-operating screw thread section.

4. A device according to claim 1, wherein the tubular vessel has a non-circular cross-section.

5. A device according to claim 4, wherein the tubular vessel has an elliptical cross-section.

6. A device according to claim 1, wherein the opening means comprise at least one puncturing element for puncturing the wall of the container.

7. A device according to claim 6, wherein said puncturing element is a hollow needle.

8. A device according to claim 1, wherein said opening means are fixed to the agitator element.

9. A device according to claim 1, wherein the opening means are provided on a plate slidingly engaged upon the second section of the shaft and arranged between the agitator element and the piston element.

10. A device according to claim 1, wherein the first component is solid particulate material, and the second component is liquid.

* * * * *